United States Patent
Steele et al.

(10) Patent No.: US 6,784,672 B2
(45) Date of Patent: Aug. 31, 2004

(54) THROUGH-LOG DENSITY DETECTOR

(75) Inventors: Philip Steele, Starkville, MS (US); Jerome Cooper, Starkville, MS (US); William Lionheart, High Peak (GB)

(73) Assignee: Mississippi State University, Mississippi, MS (US)

( * ) Notice: Subject to any disclaimer, the term of this patent is extended or adjusted under 35 U.S.C. 154(b) by 0 days.

(21) Appl. No.: 10/171,977

(22) Filed: Jun. 17, 2002

(65) Prior Publication Data

US 2003/0001595 A1 Jan. 2, 2003

Related U.S. Application Data

(60) Provisional application No. 60/298,118, filed on Jun. 15, 2001.

(51) Int. Cl.[7] .............................................. G01R 27/26
(52) U.S. Cl. ...................................... 324/663; 324/691
(58) Field of Search ............................... 324/662, 663, 324/664, 667, 671, 683, 691, 693, 699, 707, 709, 713, 649; 428/114, 212, 535, 537.1; 144/3.1, 39, 357, 363

(56) References Cited

U.S. PATENT DOCUMENTS

| | | |
|---|---|---|
| 3,549,986 A | 12/1970 | Prine |
| 3,805,156 A | 4/1974 | Norton et al. |
| 4,123,702 A | 10/1978 | Kinanen et al. |
| 4,500,835 A | 2/1985 | Heikkila |
| 4,617,939 A | 10/1986 | Brown et al. |
| 4,972,154 A * | 11/1990 | Bechtel et al. .............. 324/663 |
| 5,130,661 A | 7/1992 | Beck et al. |
| 5,272,624 A | 12/1993 | Gisser et al. |
| 5,585,732 A * | 12/1996 | Steele et al. ................ 324/663 |
| 5,588,429 A | 12/1996 | Isaacson et al. |
| 5,602,486 A * | 2/1997 | Novak ......................... 324/671 |
| 6,026,173 A | 2/2000 | Svenson et al. |
| 6,029,522 A | 2/2000 | Schafer et al. |
| 6,489,784 B2 * | 12/2002 | Adams et al. .............. 324/664 |
| 2002/0135385 A1 * | 9/2002 | Magill ......................... 324/663 |

FOREIGN PATENT DOCUMENTS

| | | |
|---|---|---|
| GB | 1 489 554 | 10/1977 |
| WO | WO 96/28741 | 9/1996 |

OTHER PUBLICATIONS

Haygreen, et al., "Chapter 6—Juvenile wood, reaction wood, and wood of branches and roots", Forest Product and Wood Science, 1982.

Peter, et al., "Theoretical Sawing of Pine Logs", Forest Products Journal, vol. 2, No. 11, 1962.

Peter, "Influence of Sawing Methods on . . . Lumber Grade Yield from Yellow–Poplar", Forest Products Journal, vol. 17, No. 11, 1967.

Tsolakides, "A Simulation Model for Log Yield Study", Forest Products Journal, vol. 19, No. 7, 1969.

Wagner, et al., "Simulated Sawing with a Chipping Hedrig", Forest Product Journal, vol. 25, No. 10, 1975.

(List continued on next page.)

*Primary Examiner*—Anjan Deb
*Assistant Examiner*—Walter Benson
(74) *Attorney, Agent, or Firm*—Piper Rudnick LLP; Steven B. Kelber

(57) ABSTRACT

A method and apparatus for detecting areas of differential density in logs, cants, timbers, poles or trees comprises applying a signal to one or more pairs of electrodes and measuring the magnitude and phase shift of the voltage, current or impedance at an output electrode. Electrodes may be arranged in a circumferential or opposed configuration depending on scanned product shape, and may be stationary or move freely but are preferably in direct contact with wood surface. Wire brush electrodes are used in some embodiments. Measurements are taken in both directions between an electrode pair. Multiple frequencies may be employed. Different electrode sizes may be used for different measurements.

84 Claims, 8 Drawing Sheets

OTHER PUBLICATIONS

Richards, et al., "Lumber Values from Computerized Simulation of Hardwood Log Sawing", USDA, Forest Service, Forest Products Laboratory, Research Paper, FPL 356, 1980.

Steele, et al., "Increased lumber value from optimum orientation of internal defects with respect to sawing pattern in hardwood sawlogs", Forest Products Journal, vol. 44, No. 3, 1994.

Zhu, et al., "A Computer Vision System for Locating and Identifying Internal Log Defects Using CT Imagery", Scanning Technology & Process Optimization, Wood Technology, Technical Insight Series, Edited by Szymani, 1999.

Kaestner, et al., "Microwave polarimetry based wood scanning", Proceedings of the 12th International Symposium on Non–Destructive Testing Wood, University of Western Hungary, 2000.

Huang, et al., "Tomographic imaging of two–component flow using capacitance sensors", Institute of Physics Publishing Co., 1989.

Plaskowski, et al., "Imagining Industrial Flows, applications of electrical process tomography," 1995.

Torgovnikov, "Dielectric Properties of Wood and Wood–Based Materials," Springer–Verlag Publishers, 1993.

Loser, et al, "Electrical capacitance tomography: image reconstruction along electrical field lines" Measurement Science and Technology, vol. 12, 2001.

Borsic, "Tomografia elettrica in bassa frequenza per il riconoscimento di discontinuità in oggetti cilindrici" Thesis for Laurea in Ingegneria Elettonica, politecnico di Torino, 1998.

Inman, Jr., "Resistivity Inversion", Geophysics, vol. 38, No. 6, 1973.

Dines, "Analysis of electrical conductivity imaging", Geophysics, vol. 46, No. 7, 1981.

Henderson, et al., "An Impedance Camera for Spatially Specific Measurements of the Thorax", IEEE Transactions on Biomedical Engineering, vol. BME–25, No. 3, 1978.

Zhu, et al., "Development of a real–time adaptive current tomograph", Physiol. Meas., vol., 15, 1994.

Kim, et al., "A prototype system and reconstruction algorithms for electrical impedance technique in medical body imaging", Clin. Phys, Physiol. Meas., vol. 8, Suppl. A, 1987.

Lidgey, et al., "Electrode current determination from programmable voltage sources", Clin. Phys. Physiol. Meas., vol. 13, Suppl. A, 1992.

Wilson, et al., "Mk3.5: a modular, multi–frequency successor to the Mk3a EIS/EIT system", Physiological Measurement, vol. 22, 2001.

White, "Development of Phase–Sensitive Electrical Impedance Tomography for the Detection of Decay in Wood", University of Manchester Institue for Science and Technology, Manchester, England, 1996.

Oakley, et al., "A low cost quantitiative reconstruction algorithm for ECT and EIT", Process Tompgraphy–95: Implementation for Industrial Processes I, vol. 6, No. 8, 1995.

Paulson, et al., "POMPUS: an optimized IET reconstruction algorithm", Inverse Problems, vol. 11, 1995.

Isaksen, "A review of reconstruction techniques for capacitance tomography", Meas. Sci. Technol., vol. 7, 1996.

Tiitta, et al., "Development of an electrical impedance spectrometer for the analysis of wood transverse moisture gradient", Proceedings of the 12th International Symposium of Non–Destructive Testing of Wood, University of Western Hungary, 2000.

Sobue, "Measurement of moisture gradient in wood by Electrode Scanning Moisture Analysis ESMA", Proceedings of the 12th International Symposium on Non–destructive Testing of Wood, University of Western Hungary, 2000.

Soest, "Internal Defect Scanning Using MRI in Combination with Automatic Pattern Recognition", Chapter Twelve, Scanning Technology & Process Optimization, Szymani, R., Ed., 1999.

Schafer, "Development of Ultrasound–Based Scanning for Wetwood and Honeycomb Detection in Hardwood Lumber", Chapter 23, Scanning Technology & Process Optimization, Szymani, R., Ed., 1999.

Savolainen, et al., "An EIT Measurement System for Experimental Use",University of Kuopio Department of Applied Physics Report Series ISSN 0788–4672, Report No. 2/96, Mar. 29, 1996.

\* cited by examiner

THROUGH-LOG DENSITY DETECTOR

This application claims the benefit of earlier-filed U.S. provisional application serial No. 60/298,118, entitled "Through-Log Density Detector" and filed on Jun. 15, 2001, the contents of which are hereby incorporated by reference herein.

This invention was made with Government support under grant number 98-34158-5869 awarded by the USDA CSREES. The Government has certain rights in the invention.

BACKGROUND OF THE INVENTION

1. Field of the Invention

This invention relates to an apparatus and method for detecting the density of logs, cants, timbers, poles or trees. More particularly, the present invention relates to the detection of anomalies such as knots in wood.

2. Discussion of the Background

Lumber is typically sorted and classified primarily on the basis of the number of knots or other defects or anomalies therein. Lumber value may be increased by theoretical detection of internal log characteristics followed by orientation of the log on the carriage. In addition, cants sawn from logs are then sent to a resaw for processing into lumber.

Bowyer and Haygreen in *Forest Products and Wood Science* (1982) note that the characteristics of certain abnormal wood types such as compression wood, tension wood and juvenile wood can result in inferior performance of the wood products they contain. Compression wood is formed on the ground side of boles leaning softwood trees; tension wood is formed on the side opposite the ground on leaning hardwood trees. Juvenile wood formed near tree pith in the first 10 to 15 years of tree growth. Compression wood may exhibit longitudinal shrinkage up to 10 times more than that of normal wood. Wood products containing both normal and compression wood exhibit differential shrinkage when dried. Warpage is the result of this differential shrinkage.

Tension wood also shrinks abnormally longitudinally with the same warpage problems resulting. When machined, tension wood often has a fuzzy surface making furniture finishes substandard. Cell collapse during drying also frequently occurs resulting in a lumber grade-reducing drying defect.

Juvenile wood has thinner cell walls with resultant lower strength properties. Lumber with low strength properties may be assigned to a lower lumber grade. For this reason restrictions on purchases of young timber have been imposed in recent years as plantation timber growth rates have accelerated.

Differential orientation of the log or cant can change the location of the defects in the lumber sawn from the log and thereby change lumber grade and resultant value. To date, research on log positioning has focused on angular orientation of the logs about their central axes. Most defects in both logs and lumber are knot defects so that most of the influence on value change results from changing knot location in lumber by rotating the log. Peter et al., *Forest Prod. J.* 2(11):47–50 (1962); Peter, *Forest Prod. J.* 17(11):19–24 (1967); Tsolakides, *Forest Prod. J.* 19(7):21–26 (1969); Wagner et al., *Forest Prod. J.* 25(10):24–28 (1975); Richards et al., Res. Pap. FPL-356, USDA Forest Serv., Forest Prod. Lab. (1980); Steele et al., *Forest Prod. J.* 44(3):69–72 (1994) have all conducted studies relating to the influence of angular orientation on increased lumber value and have indicated increases ranging from 9 percent to 21 percent for hardwood and 7.5 percent for southern yellow pine. All of these referenced studies, however, involved some form of computer simulation of the sawing process to determine increased lumber value.

Application of various technologies to perform internal log scanning have been pursued. For example, Szymani, *Scanning Technology and Process Optimization: Advances in the Wood Industry*, Miller Freeman Books (1999), discloses attempts at X-ray, NMR and ultrasound log scanning. A basic presumption for the application of internal log scanning to log sawing is that the knowledge of internal defects will lead to choosing the best sawing position and method and, therefore, will allow sawmills to realize potential gain. Development of devices for internal log scanning, however, requires solving numerous technical and cost problems before industrial application is feasible.

Shafer and Ross (2000) have disclosed, in U.S. Pat. No. 6,029,522, an ultrasonic device that allows detection of localized anomalies such as knots, decay and voids in logs. Multiple measurements allow generation of maps of anomaly location such that sawing decisions can position sawlines to produce lumber with maximum value. Haddox, *Wood Technology* 127(2):22–27 (2000), reports a commercial installation of an ultrasound cant scanner.

A number of patents and publications, for example, U.S. Pat. No. 3,549,986 to Prine, U.S. Pat. No. 4,123,702 to Kinanen et al., U.S. Pat. No. 4,500,835 to Heikkila et al., British Patent Specification No. 1,489,554 and Finnish Patent Publication No. 53,365, disclose the use of microwaves to detect knots or slope of grain. Other patents such as, for example, U.S. Pat. No. 4,972,154 to Bechtel et al., U.S. Pat. No. 3,805,156 to Norton et al. and U.S. Pat. No. 5,585,732 to Steele and Kumar, disclose devices that employ radio frequency waves to detect knots or slope of grain in lumber. Neither the microwave nor the radio frequency lumber scanning devices describe the ability to detect knots or other types of density differences in logs, cants, timber, poles or trees.

Kaestner et al., *Microwave Polarimetry-Based Wood Scanning*, Proceedings of the 12$^{th}$ International Symposium on Non-Destructive Testing of Wood, September 13–15, University of Western Hungary (2000), describe a device that employs a waveguide that both transmits microwaves and receives the reflected waves in the range of 4 to 8 GHz. The researchers employed analysis of the polarized signal because attenuated signals from surfaces within the log were so weak as to be difficult to identify. Internal knots and other density-related areas in scanned log sections were able to be delineated in the tomographic slices produced by this microwave scanning device. This Kaestner et al. device differs from the TLDD in that microwaves rather than radio frequency signals are employed to detect density-based anomalies. Wave guides are employed as sending and receiving transducers by the Kaestner et al. device while the TLDD employs electrodes as sending and receiving transducers.

A number of references disclose the use of computer tomography imaging in combination with technology such as X-ray technology to detect anomalies in logs. For example, U.S. Pat. No. 6,026,173 to Svenson et al. discloses a microwave tomographic device to detect dielectric property differences within biologic tissue. Multiple receiving and transmitting waveguides are arranged in a ring, and the object to be scanned is placed within the circular array. Multiple frequencies are transmitted through the tissue in frequencies ranging from 0.1 to 300 GHz by opposing transmitting and receiving waveguides. Signal analysis of the multiple frequency response to dielectric differences within the tissue allows imaging of the structures responsible for these differences. As with the Kaestner et al. device, the Svenson device employs microwaves transmitted and received with wave guides. This differs from the TLDD in that radio frequency signals are transmitted and received with electrodes.

Huang et al., *Tomographic Imaging of Two-Component Flow using Capacitance Sensors*, Institute of Physics Publishing Co. (1989), and U.S. Pat. No. 5,130,661 to Beck et al. describe the development of a laboratory prototype of a capacitance electrode scanner for performing application of Electrical Capacitance Tomography (ECT) to obtain images of two-component fluids flowing through pipes. The device consists of an eight-electrode capacitance sensor in which the 8 electrodes are arranged equidistant from each other on the external periphery of the circular pipe through which the fluid flows. The capacitance of a 2 MHz radio frequency signal is measured between all possible pairs of the 8 electrodes. An image of the respective area occupied in the internal cross section of the pipe by each component of the two-component fluid flow is developed. This is accomplished by computer reconstruction of the measured capacitance values with a linear back-projection algorithm.

Plaskowski et al. in their book *Imaging Industrial Flows: Applications of Electrical Process Tomography* (1995) describe ECT technology in considerable detail. This technology applies electrodes to measure the cross-sectional capacitive components of a radio frequency signal transmitted across pipe diameter or across similarly circular-shaped cross sections. The original goal of the ECT technology was to differentiate the components of two-component non-conducting fluids flowing in a pipe. The capacitor electrodes employed by ECT are relatively large in comparison to the cross sectional diameter of the scanned medium because of the low conductivity of the medium. In the 8-electrode system, described as an example, electrode length was given as 110 mm or 1.2 times the pipe diameter of about 92 mm. The capacitance electrodes are required to be of large area because of the low signal levels they are required to sense. For the described example the 8-electrode system with 110 mm wide electrodes has a minimum standing capacitance of about 0.3 pF between electrodes positioned opposite each other and separated by the pipe diameter.

Torgovnikov, in *Dielectric Properties of Wood and Wood-Based Materials* (1993), classifies wood as having a conductance below that of semiconductors even when it is of maximum moisture content. Therefore, wood is considered to be non-conductive.

By the ECT method a radio frequency signal is applied to a single electrode while all remaining electrodes are grounded and act as receiving electrodes. Loser et al. *Meas. Sci. Technol.* 12:1083–1091 (2001) describe the two alternative ECT methods for grounding and acquiring signal data from non-sending electrodes. By one method all non-sending electrodes are grounded and signal information can be acquired from all simultaneously but with discrete values obtained from each receiving electrode. By a second method, only one receiving electrode is grounded at a time and signal information is acquired at that time, as described by Loser et al., *Meas. Sci. Technol.* 12:1083–1091 (2001).

For the 8-electrode example, as previously described by Huang et al. and Beck et al., the total number of possible electrode combinations is 28. Neither Huang et al., Beck et al. nor Plaskowski et al. indicate that bi-directional electrode query is important to the accuracy of their apparatus.

The capacitance electrodes described by Plaskowski et al. for ECT technology are not in direct contact with the medium being scanned. Rather, the electrodes are in contact with the pipe surface and are separated from the medium by the pipe wall thickness. In this sense, these electrodes are non-contacting electrodes. The ECT electrodes are necessarily fixed in place as they must be in direct contact with either the pipe or similar sleeve surface.

The ECT devices described by Huang et al., Beck et al. and Plaskowski et al. differ markedly from the TLDD in several ways. The ECT electrodes are large relative to the diameter of the medium being scanned to increase their sensitivity. The TLDD electrodes are small in area compared to the diameter of the medium scanned. For example, TLDD electrodes may be 1" long and may be separated by a diameter of scanned medium by 20" or more. The capacitor-to-diameter ratio for this example is 0.05 compared to 1.2 for the ECT example given by Plaskowski et al. The ECT electrodes are non-contacting while those of the TLDD are in direct contact with the medium. By one ECT method, all electrodes other than the sending electrode are grounded; by a second ECT method only one receiving electrode is grounded at a time while other electrodes are not grounded. The receiving TLDD electrode(s) are grounded in both ECT methods described above. In addition, the TLDD receiving electrode(s) may not be grounded when measuring voltage or impedance. In addition, for ECT the electrodes are fixed while for the TLDD the electrodes may move freely as long as direct contact with medium surface is maintained. For ECT scanning the signal applied is limited to a radio frequency signal and the voltage is measured at the receiving electrode. For the TLDD, the applied signal may be a radio frequency signal, and the received signal may be measured as voltage, impedance or current. Also, by the ECT method only signal magnitude is measured while the TLDD measures both signal magnitude and phase shift. For ECT bi-directional electrode sensing is not an issue while for the TLDD, when voltage is measured at the receiving electrode, this bi-directional sensing is important in locating anomalies and determining their size and location. Therefore, for TLDD voltage measurements the total number of electrode pair combinations is double that for ECT because bi-directional electrode query is employed.

Plaskowski et al. (1995) describe technology termed Electrical Impedance Tomography (EIT) that is similar to ECT in some respects. However, EIT is designed for scanning electrically conductive materials. This allows its use for scanning water-based fluids flowing in pipes as well as for medical imaging of some types of tissue. As previously discussed, ECT has been developed to scan relatively non-conducting materials such as oil-based fluids flowing in pipes. A discussion of the detection of rot in living trees using EIT has been reported by A. Borsic, *Tomografia elettrica in bassa frequenza per il riconoscimento di anomalie in corpi cilindrici*, Thesis for Laurea in Ingegneria Elettonica, Politecnico di Torino, 1998.

A variety of electrical imaging methods have been reported in the literature where measurements of transfer impedance using a system of electrodes external to a body are used to deduce the interior electrical properties (conductivity and permittivity). The earliest use is geophysical resistivity imaging, as reported for example by, Inman et al. *Geophysics*, 38:1088–1108 (1973) and by Dines and Lyle, *Geophysics*, 46 (7): 1025–1036 (1981). Application to imaging of the human body followed initiated by Hendersen, *IEEE Biomed. Engr. Trans.* 25 (3): 250–254 (1978), and realized in a practical form by Brown and Barber in U.S. Pat. No. 4,617,939 by employing the medical technique originally called Applied Potential Tomography APT, now mostly called Electrical Impedance tomography, EIT. Similar methods were later applied to imaging of industrial processes. Beck et al. used non-contact measurements of mutual capacitance to image permittivity of insulators. Later the Barber and Brown EIT method was applied to conductive media in process monitoring where the technique is called Electrical Resistance Tomography (ERT).

Given a system of N electrodes, reciprocity dictates that there are N(N-1)/2 independent measurements of mutual impedance that can be made. A complete set of measurements requires the application of a set of N-1 independent current patterns and the measurement of the voltages induced on the electrodes, or conversely the application of a set of N-1 independent voltage excitation patterns and the measurement on the corresponding currents. If the impedance of the medium is complex then the complex current and voltage must be known.

There are many possible measurement strategies. The excitation of current in pairs of electrodes in turn is usual in geophysical imaging, medical EIT and industrial ERT. Multiple current generators are used to drive optimal current patterns as described by Gisser's U.S. Pat. No. 5,272,624, Isaacson's U.S. Pat. No. 5,588,429 and as in the system OXBACT III described by Zhu et al. *Physiological Measurements* 15: (A37–A43)(1994). Multiple voltage drive systems have also been devised, for example the system discolosed by Kim, *Clin. Phys. Physiological Measurements* 8: 63–70 (1987), and the OXPACT II system described by Lidgey et al., *Clinical Physics and Physiological Measurements*, 13: 43–46 (1992). ECT systems typically use a voltage drive strategy where one electrode is excited with a given voltage and the current through the others measured to a virtual ground. The measurement can use a square wave excitation and charge transfer measurement circuit, or sine wave excitation as used in EIT. Medical EIT systems have been devised by *Physiological Measurements* 22:49–54 (2001) to employ multiple frequencies to characterize tissue properties.

White discloses an ECT device that can be used for detecting rot in wood in his 1996 dissertation titled *Development of Phase-Sensitive Electrical Impedance Tomography for the Detection of Decay in Wood*, University of Manchester Institute for Science and Technology, Manchester, England. White's device employed the ECT method described above in which all non-sending electrodes are grounded and signal information is acquired from all non-sending electrodes simultaneously.

The White device employed non-contacting electrodes to measure electrical loss as a result of presence of decay in wooden power poles. Eight electrodes were strapped around pole circumference on a flexible belt. Current was measured by applying a radio frequency voltage at 500 KHz to a single electrode and measuring the current flowing to the other seven electrodes. The current was demodulated to measure magnitude and phase shift. A tomographic image of the decay pattern within the scanned cross sectional slice was then reconstructed.

White discussed the relative non-conductance of wood as his reason for adopting a typical ECT system approach. He employed large electrodes similar to those applied to relatively non-conducting fluids such as oil in pipes. The White device is similar to a typical ECT system in that the impedance of the signal transmitted between electrodes is measured. However, the White device measures both current magnitude and phase shift rather than only magnitude as Plaskowski et al. describe for typical ECT technology. White employs measuring only two-dimensional data in his described method. This approach may lead to significant errors in anomaly detection.

The White device differs from the invention in several respects. The White device differs from the TLDD in that the TLDD electrodes are in direct contact with the medium and those of the White device are non-contacting. The TLDD device may measure the voltage at each electrode of each possible electrode pair and may measure the impedance and/or current in both directions between each possible electrode pair. In contrast, the White device does not measure voltage at the receiving electrode. Because bi-directionality of transmission is an issue only for voltage in voltage out systems, White did not consider bi-directionality.

White also measures only a single signal frequency rather than employing multiple frequencies to improve anomaly detection as is employed by some embodiments of the TLDD. White employs only a single series of circumferential electrodes as opposed to the TLDD's use in some embodiments of a multiplicity of circumferentially arranged electrodes for obtaining three dimensional data. White makes no provision for free-moving electrodes to accommodate a wood product of variable shape moving at speed between electrodes as is the case for the TLDD. White does not provide for use of electrodes of varying size and/or shape to improve their sensitivity to different anomaly sizes. Finally, White's method is not amenable to application of the more accurate three-dimensional ECT methods while the motion of objects by the TLDD method will allow this application.

Oakley et al., *Process Tomography-95: Implementation for Industrial Processes* I(6–8):393–400 (1995), Paulson et al., Inverse Problems 11:425–437 (1995) and Isaksen, *Measurement Science and Technology* 7:325–337 (1996) disclose several ECT algorithms that allow reconstruction of a two-dimensional tomographic image based on sensed differences in material capacitance. Plaskowski et al. (1995) describe both ECT and EIT algorithms for reconstruction of two-dimensional tomographic images. Therefore, the algorithms and software techniques for reconstruction of images from data from multiple dielectric signals passed between pairs of electrodes are well documented. Some adaptation of these techniques is expected to suit them for application to the TLDD dielectric data.

Venter and Viljoen, in International Patent Number WO 96128741, titled Determining the Dielectric Properties of Wood describe a device for measuring the moisture content of a stack of lumber during kiln drying. Large electrode plates are placed across several pieces of lumber. In the example illustrated in the patent, a second lower electrode, of the same size and shape, is also placed across several courses of lumber but with seven layers of wood and six layers of air between it and the upper electrode. The lower electrode is grounded and radio frequency signal is applied to the upper electrode. The electric signal passes through the alternate layers of wood and air to the lower electrode and the magnitude and phase shift of the signal are measured as the wood is dried by the heat in the dry kiln.

The circuit to accomplish this application includes a signal generator connected to a load driver that imposes the radio frequency signal to a resistor. The load driver is required to allow the radio frequency signal to be driven across the high resistance created by the multiple layers of wood and air in the drying lumber. The Venter and Viljoen device measures moisture changes in the lumber between the electrodes as related to the difference in the input voltage denoted $v_1$ and the voltage transmitted through the lumber and air courses which is denoted $v_2$. This difference allows a direct determination of the increasing magnitude and an indirect computation of the phase shift that occurs as wood moisture content decreases during kiln drying. These voltage $v_1$ is measured prior to the resistor and $v_2$ just after the resistor.

The only variable wood characteristic that the Venter and Viljoen device is described as detecting is moisture content. No application of the device to determine density differences to detect anomaly presence is reported.

Steele and Cooper have disclosed a patent titled Moisture and Density Detector (Pending) for sensing moisture and/or density differences in wood or other dielectric materials. The Moisture and Density Detector (MDD) circuits measure dielectric values of magnitude and phase shift. The potential use of the MDD to detect wood types is disclosed, but detection of localized anomalies such as knots, voids, decay, etc. are not. In addition, the MDD electrodes are directly opposed to scan through wood thickness or are directly adjacent for scanning horizontally across wood surface. No disclosure of a circular electrode arrangement to detect anomalies in logs, poles, trees, or thick materials such as cants or timbers is made. The Steele and Cooper device also employs only voltage magnitude and phase shift measurements but not impedance magnitude and phase shift. No consideration is given to bi-directional electrode query to allow better detection of anomaly position between electrode pairs. The MDD directly opposed or directly adjacent electrode positioning is intended to allow scanning through relatively flat objects such as lumber or a thin flat layer of dielectric materials such as chips carried on a conveyor.

An impedance detector disclosed by Tiitta et al., *Development of an Electrical Impedance Spectrometer for the Analysis of Wood Transverse Moisture Gradient*, Proceedings of the 12$^{th}$ International Symposium on Non-Destructive Testing of Wood, September 13–15, University of Western Hungary (2000), measures the moisture gradient in wood. Tiitta et al. termed this method spectral impedance. By this method, electrodes contained in a probe were placed on the wood surface. One electrode transmitted an electrical signal at frequencies below 5 MHz, and the second received the signal. A variable electric field was developed between the electrodes. Analysis of the behavior of impedance for the various frequencies transmitted through the wood allowed estimation of the moisture gradient within the wood. This technique of spectral impedance has not been used to detect anomalies in wood.

Sobue, *Measurement of Moisture Gradient in Wood by Electron Scanning Moisture Analysis (ESMA)*, Proceedings of the 12$^{th}$ International Symposium on Non-Destructive Testing of Wood, September 13–15, University of Western Hungary (2000) discloses paired electrodes in the radio frequency range to detect the moisture gradient in wood. Rather than vary frequency and analyze the impedance spectrum as did Tiitta et al., Sobue varied the distance between the electrodes. This distance variance modified the capacitance of the signal. Sobue analyzed the signal behavior for the several capacitances produced and estimated moisture gradient based on this analysis. Sobue did not employ this device to detect anomalies in wood.

A need, therefore, exists for devices and methods for detecting anomalies as evidenced as locations of differential density in logs, cants, timbers, poles or trees using dielectric signals passed through the wood comprising these products.

SUMMARY OF THE INVENTION

It is an object of the present invention to provide a method and apparatus for determining the density of logs, cants, timbers, poles, or trees.

It is another object of the present invention to provide a method and apparatus for detecting localized anomalies, such as knots, in logs, cants, timbers, poles, or trees.

These and other objects of the invention are achieved by a method and apparatus for detecting areas of differential density in logs, cants, timbers, poles, or trees and the like to determine anomalous internal characteristics such as knots, voids, decay, and wood type. The method comprises applying signals to one electrode attached to the wood piece and measuring the output at a plurality of other electrodes in contact with the wood piece. Preferably, the transmitted signal is applied to each electrode of an electrode pair (sometimes referred to herein as bi-directional electrode query) in order to detect smaller anomalies such as knots. The signal transmitted to the sending electrode is preferably a radio frequency signal. The signal received at the receiving electrode may be measured as voltage, impedance or current. The magnitude and/or phase of each signal type may be measured. The data from combinations of all possible pairs of electrodes is analyzed to determine a location of an anomaly. Location, depth and area of anomaly may be estimated. Alternatively, tomographic techniques, such as those currently employed for EIT, may be applied to develop an image of density differences in the scanned cross-sectional data. Such techniques are well known in the art and will not be discussed in further detail herein.

One embodiment of the invention comprises multiple pairs of electrodes disposed at predetermined angles to each other. Electrodes may be of any size or shape and are in direct contact with wood surface. Electrodes may move freely to accommodate the differentiated shape of the wood product passed between them. Adjustments are made for electrode displacement as electrodes move with respect to each other.

Measurements at electrodes may be made sequentially or simultaneously. When measuring voltage or current at a particular electrode, or when measuring impedance between a pair of electrodes, electrodes other than the electrode to which the input signal is applied and the particular electrode at which the measurement is being taken, or other than the electrodes between which impedance is being measured, may be grounded or ungrounded. When measuring current at an electrode, that electrode should be grounded. Determination of both magnitude and phase shift of the voltage, impedance, and current signals may be performed to provide additional information. Any circuit allowing measurement of current, voltage and impedance may be utilized for the apparatus.

The above and other objects and advantages of the present invention will become more apparent from a reading of the following detailed description of the invention in conjunction with the drawings and the appended claims.

DETAILED DESCRIPTION OF THE INVENTION

The present invention is directed to a method and apparatus for detecting areas of differential density in wood to determine internal characteristics in the form of anomalies. These anomalies may be knots, voids, decay, or wood types. The wood types may be compression, tension, juvenile or others. The invention will be discussed below in connection with certain preferred embodiments of the invention. Numerous details, such as specific equipment, numbers of electrodes, etc., are set forth in order to provide a thorough understanding of the present invention. The preferred embodiments discussed herein should not be understood to limit the invention. Also, method steps described herein should not be understood to be necessarily independent or order-dependent in their performance.

Figure 1:
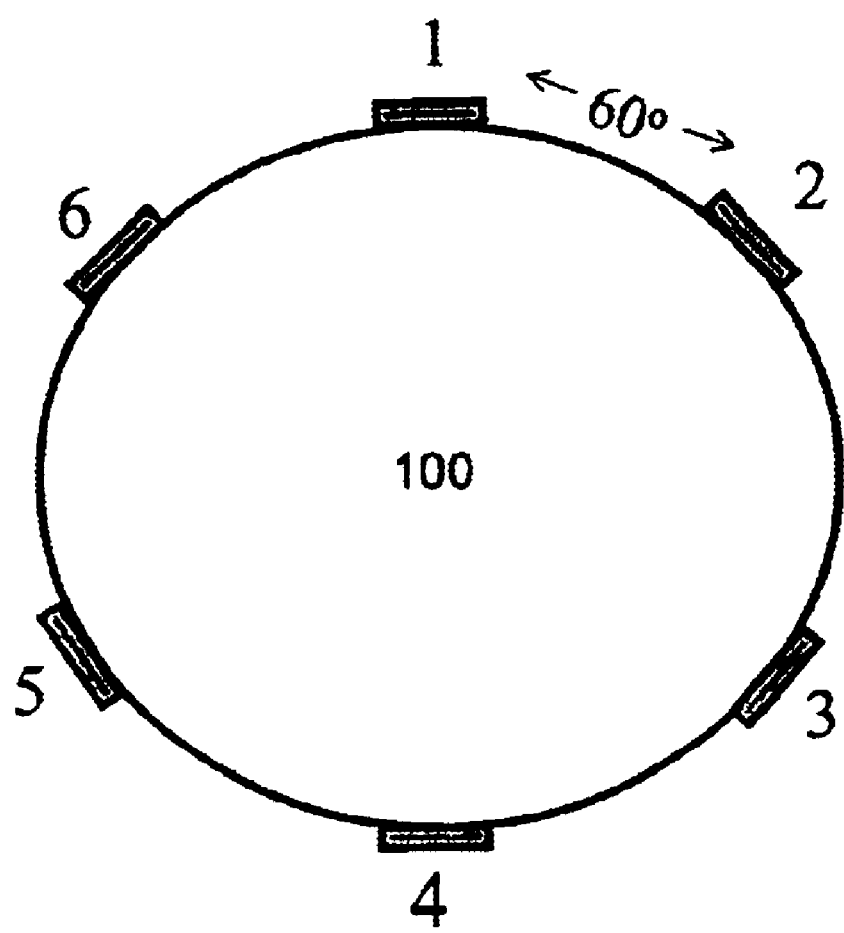
FIG. 1 is a schematic of an example of circumferentially arranged electrodes positioned to scan a log, pole or tree.
Figure 2:
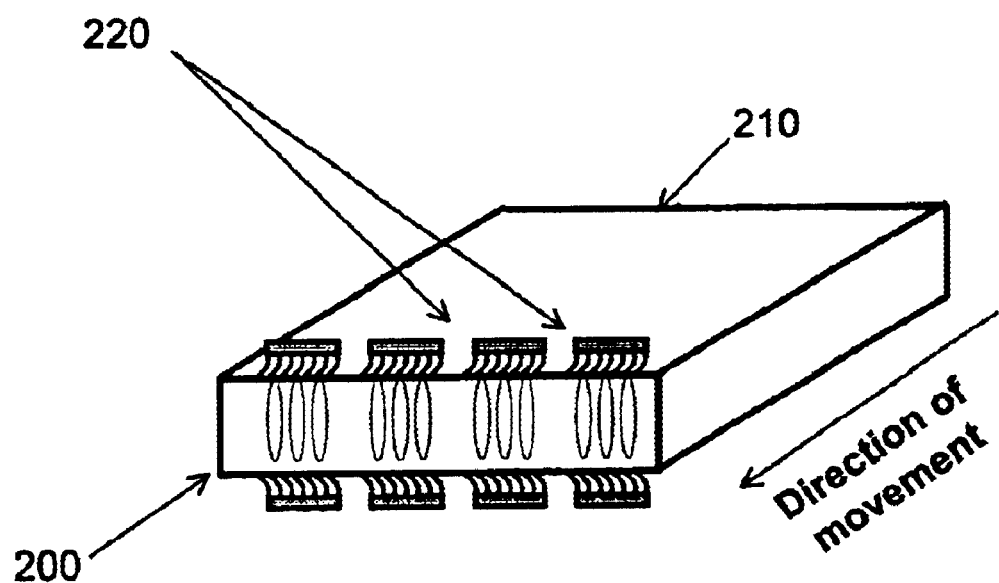
FIG. 2 is schematic end view of opposed electrodes positioned to scan a timber or cant.

One embodiment of the invention employs ECT technology and comprises a dielectric scanner utilizing multiple pairs of electrodes disposed at predetermined angles to each other. FIG. 1 illustrates a circular arrangement of sensors 1–6 around a wood piece 100 such as a log, pole or tree. For wood pieces 200 such as cants or timbers, electrodes 220 are preferably arranged in an opposed configuration in contact with the upper surface 210 and the lower surface (not shown in FIG. 2) of the wood piece 200 as shown in FIG. 2. When the between-electrode signal is measured in terms of voltage or impedance, the magnitude and phase shift of the signal may be measured. When the between-electrode signal is measured as current, the magnitude is measured while the phase shift may be computed based on known relationships. Some embodiments of the present invention compensate for electrode movement resulting from variations in wood dimension and for varying distances between electrodes.

In embodiments of the present invention for use in scanning variably shaped wood pieces, the electrodes are movable and/or are flexible (e.g., wire brush electrodes). However, the need for large amounts of movement may be reduced by practicing log sorting. This method, which is frequently used in Europe but is infrequently practiced in North America, allows segregation of logs into diameter classes prior to sawing. This allows individual diameter classes to be processed with minimum or no adjustment of saws to apply the best sawing solution. Likewise, for the TLDD, log sorting would allow application of a scanning head that may need only to accommodate plus-or-minus 1 inch or so of movement to accommodate log taper and bumpiness. Changing the scanner head for each diameter class would be required to allow this method to be practiced.

The electrodes of the apparatus of the present invention are preferably in direct contact with the wood being scanned. For voltage and impedance measurement, the TLDD electrodes may be grounded or ungrounded. For current measurement, the receiving electrode(s) are grounded. The method of the present invention comprises applying a signal to an electrode and measuring the magnitude and phase of the signal at a receiving electrode(s). The voltage, impedance, or current may be measured. For multiple pairs of electrodes, signals between all possible pairs of electrodes are measured. Applicants' experimental results have shown that, for voltage measurements, bi-directional electrode query provides important information regarding anomaly position. When using bi-directional electrode query, the number of unique electrode pairs is double that for single-direction electrode query.

The magnitude and phase shift information between electrode pairs is analyzed to allow detection of anomalies in the cross-sectional area scanned. An image of the cross-sectional data may be developed with tomographic algorithms, based on regularized Newton's method or other numerical techniques.

Figure 5:
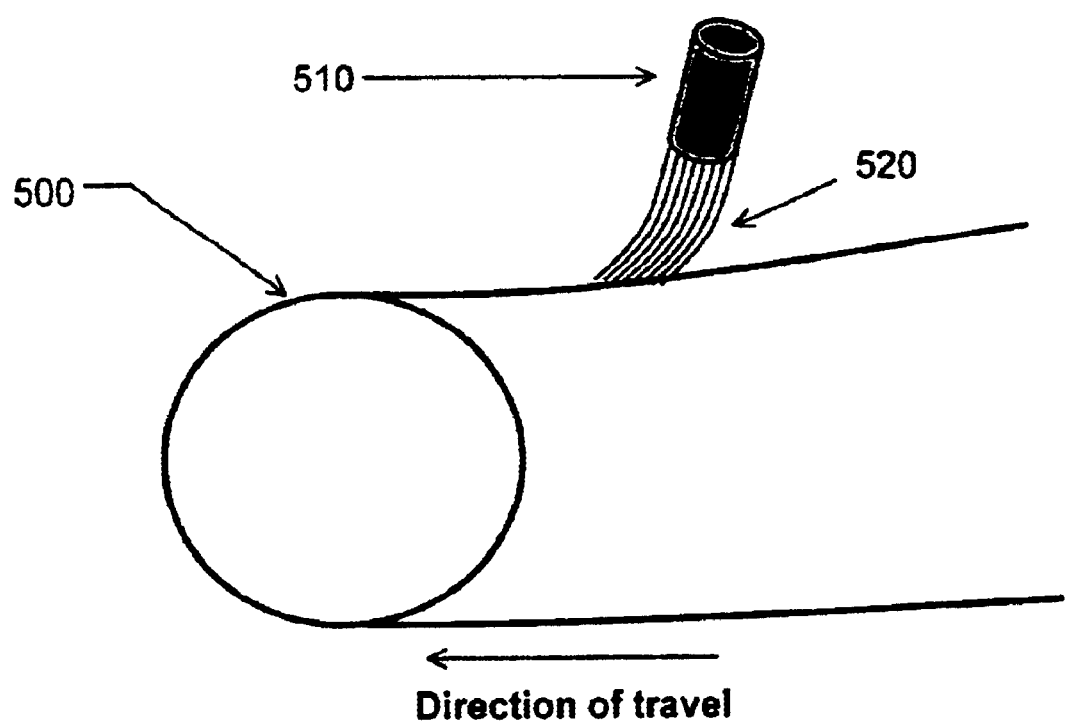
FIG. 5 is a side view of a wire brush electrode according to an embodiment of the invention.

Electrodes of the TLDD are preferably in direct contact with the scanned medium. Electrodes may be constructed of any conductive material and may be of any shape and size (however, as discussed further below, electrode size should be reduced as the size of anomalies that are desired to be detected is reduced). Steel, stainless steel, and aluminum materials have been tested. Circular electrodes of various diameters have been tested. Rectangular electrodes have also been tested. Electrodes may be rigid or flexible. Good results however, have been obtained with flexible aluminum circular electrodes backed with a thin foam material that allows conformance of the electrode to the log surface. These types of electrodes are suitable to stationary detection of defects which may be particularly useful for scanning trees or poles that are scanned on site. In some embodiments of the invention used when wood pieces such as the sawlog 500 of FIG. 5 are in relative motion with respect to the electrodes, electrodes are in the form of a wire brush 510. The wire brush tips 520 of the wire brush 510 have been found to conform well to a log surface and to provide good signal conductance when the sawlog 500 is moved relative to the wire brush 510. Other electrode designs that allow the scanned wood object to move between electrodes, while maintaining electrode contact, may be applied. Electrodes may be held to a log surface in any manner such as by arms, on a rotating wheel, etc.

The TLDD of the present invention passes a signal between electrode pairs. The magnitude and/or phase shift of the received signal indicates the density of the wood between the electrodes. As discussed above, FIG. 1 illustrates a preferred orientation of electrodes in the TLDD of the present invention. As seen therein, the preferred orientation of electrodes for detecting anomalies in logs, poles or trees is a circular orientation with electrodes are placed at sixty degree increments around the circumference of the wood piece. The minimum number of electrodes is 2. The number of electrodes may be more or less than 6. For wood products such as cants or timbers, electrode orientation will be in an opposed configuration as shown in FIG. 2.

Electrodes that conform to log surface will provide strongest signal through the dielectric material. Signals have been successfully transmitted between pairs of sensors placed at 60, 120 and 180 degrees of arc increments. For example, signals have successfully been transmitted between electrodes across 180 degrees of arc, which corresponds to transmission from Electrode 1 to Electrode 4 in FIG. 1. Likewise, signals have been transmitted across 120 degrees of arc corresponding to sending a signal from Electrode 1 to Electrode 3 in FIG. 1. Signals have also been transmitted across 60 degrees of arc corresponding to sending a signal from Electrode 1 to Electrode 2 of FIG. 1. The electrodes are preferably directly applied to the surface of the wood being measured and conform closely to the wood surface shape in highly preferred embodiments.

Figure 4:
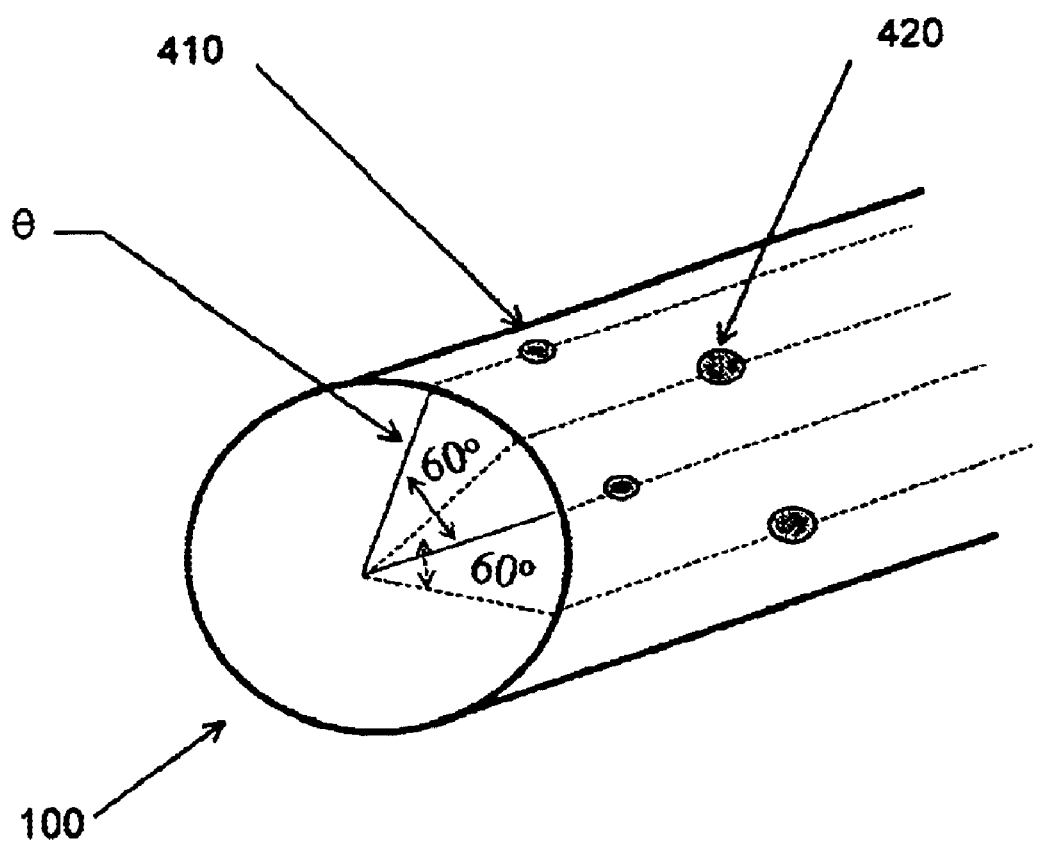
FIG. 4 is a perspective view of a log having a plurality of electrodes placed around the circumference thereof according to an embodiment of the invention.

It may also improve TLDD performance to use additional circumferential series of electrodes. The electrodes of the second and following electrode series may be oriented in any angular orientation, but preferably will be oriented such as to divide circumferential segments between initial adjacent electrodes. An example of such an arrangement is shown in FIG. 4, wherein electrodes 410 (represented by a circular shape) of a first electrode series are spaced in increments of an angle θ of 60 degrees around a circumference of a scanned wood piece 100, electrodes 420 of a second series (represented by a rectangular shape) are also spaced at 60-degree increments, and the angular distance between neighboring electrodes of the first and second series is 30 degrees.

The electrode in the second, or subsequent, circumferential electrode series will perform as described for a single series. However, if small anomalies (such as knots) and larger anomalies (such as areas of decay) are both to be detected by a single system, it may be desirable to employ larger-sized electrodes in one series 420. In addition, electrodes of two or more series may transmit a dielectric signal between electrode pairs of these second series. Potentially, data from all possible electrode pairs between the series, with bi-directional electrode query, will be obtained.

Figure 3:
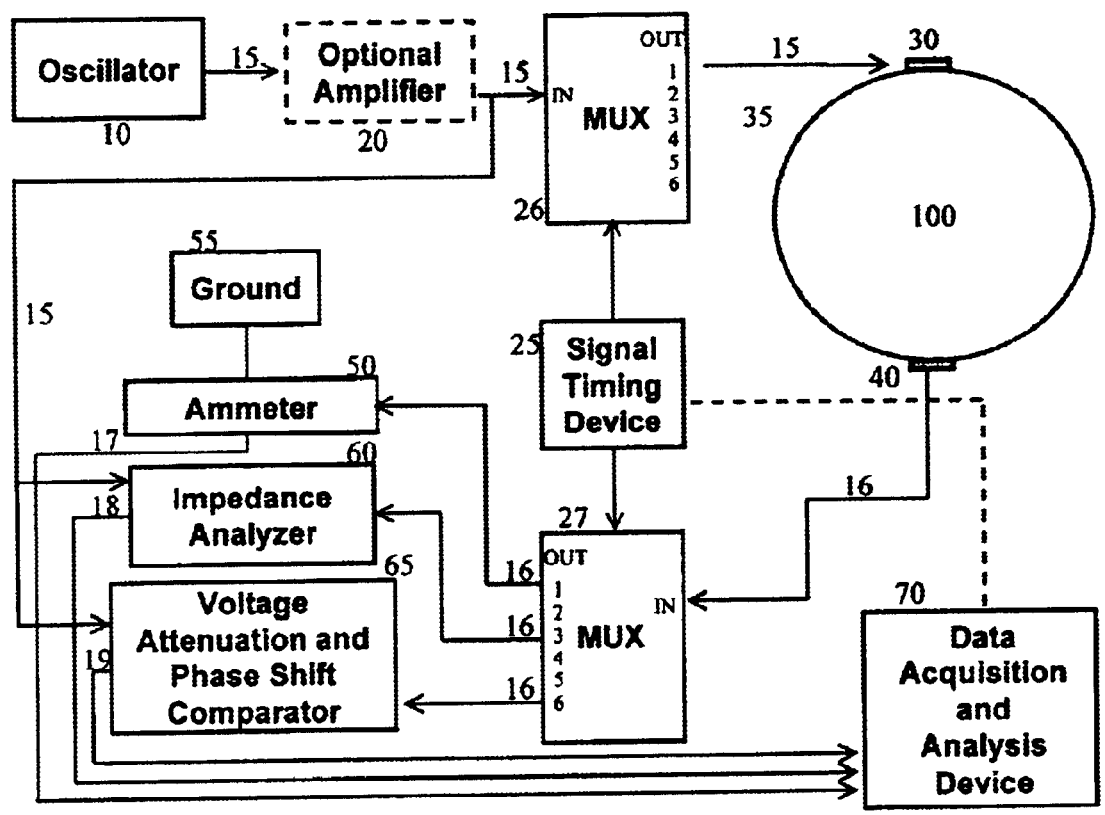
FIG. 3 is a block diagram of the components of the through-log density detector of the present invention in one embodiment of the present invention.

FIG. 3 shows the basic components comprising a TLDD according to some embodiments of the invention. Only two electrodes are illustrated in FIG. 3 to simplify illustration of the concepts involved; however, more than two electrodes may be employed. An oscillator 10 generates a radio frequency signal 15 which may be amplified by an amplifier 20 to increase signal strength. This signal 15 is connected to the input of a multiplexer 26. The first multiplexer 26 is controlled by a signal timing device 25, which causes the signal 15 to be applied one of the outputs of the first multiplexer 26, which is the output connected to electrode 30 as shown in FIG. 3. Electrode 40, which is placed on the opposite side of the wood piece 100, is connected to the input of the second multiplexer 27. The second multiplexer 27 is controlled by the signal timing device 25 to output the signal from the electrode 40 to either the ammeter 50, the impedance analyzer 60, or the voltage attenuation and phase shift comparator 65. The values measured by the ammeter 50, the impedance analyzer 60, and the voltage attenuation and phase shift comparator 65 are input to a data acquisition and analysis device 70, which also receives control and data signals from the signal timing device 25 so that data is collected from the appropriate device at the appropriate time. The data acquisition and analysis device 70 may construct tomographic images of the wood piece 100 in some embodiments. When the signal timing device 25 calls for measurement of current by the ammeter 50, the electrode 40 is connected to the ground 55 through the ammeter 50. When measuring current, the ammeter 30 will measure current magnitude. Phase shift may be computed based on known relationships or a circuit may be employed for this purpose. When the signal timing device calls for measuring impedance or voltage, the electrode 40 need not be connected to ground.

It should be understood that, although not shown in FIG. 3, the other output terminals of the multiplexer 26 are connected to the other electrodes (electrode 40 in FIG. 3 and all other electrodes in embodiments with more than two electrodes) so that the signal timing device 25 can cause the signal 15 to be applied to each of the electrodes. Similarly, the other electrodes (electrode 30 in FIG. 3 and other electrodes in embodiments with more than two electrodes) will be connected to multiplexers so that they may be connected to the measurement devices.

Numerous circuit designs may be employed to apply and measure sending and receiving in terms of the magnitude and phase of voltage, impedance, and current. It is understood that such design changes would be obvious modifications of the TLDD system.

For example, Applicants have found it useful to incorporate a load drive into their circuit in a manner similar to that described by Venter and Viljoen. This load is necessary to match the impedance of the scanned medium such that the signal will transmit through the medium. Alternatively, Applicants have also transmitted the radio frequency signal without this load driver. Applicants have measured voltages as $v_1$ and $v_2$ at the input and output of a resistor as described by Venter and Viljoen. Alternatively, Applicants have not employed a resistor and have measured input voltage and impedance at the sending electrode and transmitted voltage and impedance at the receiving electrode. Numerous methods of successfully transmitting a signal through the medium and measuring the applied and transmitted signal can be imagined.

Figure 6:
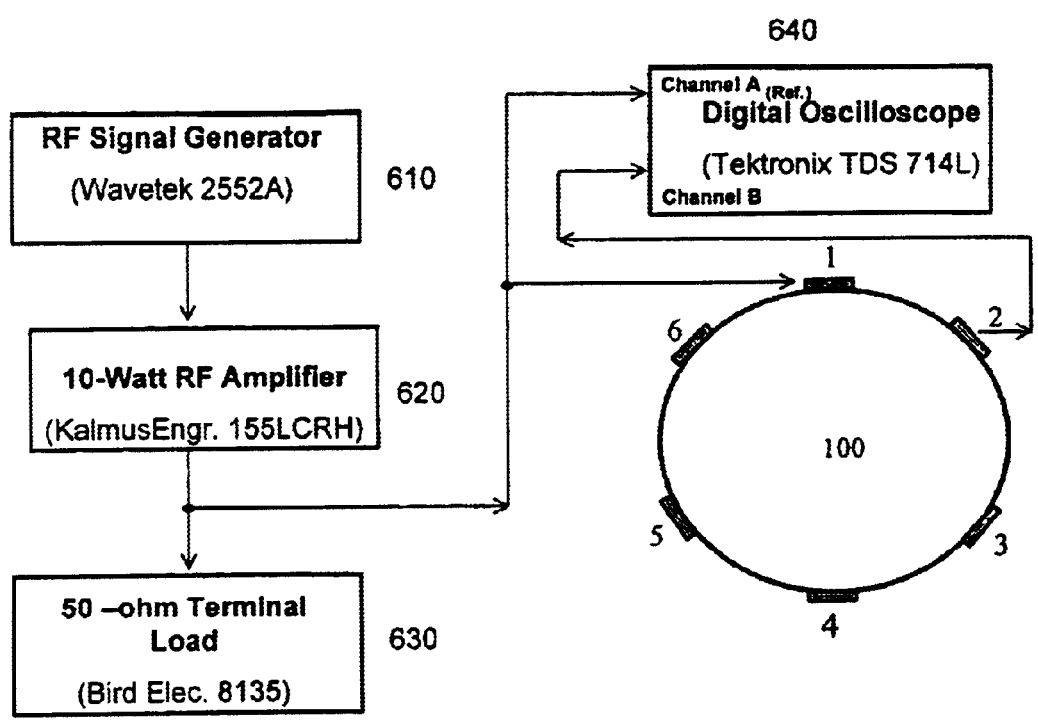
FIG. 6 is a block diagram of a voltage measurement circuit according to an embodiment of the invention.
Figure 7:
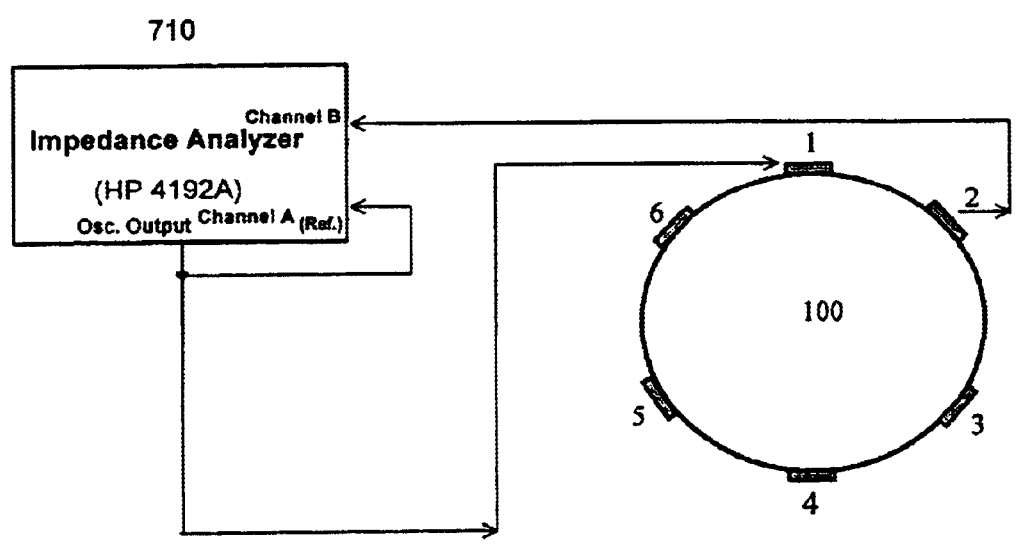
FIG. 7 is a block diagram of an impedance measurement circuit according to an embodiment of the invention.
Figure 8:
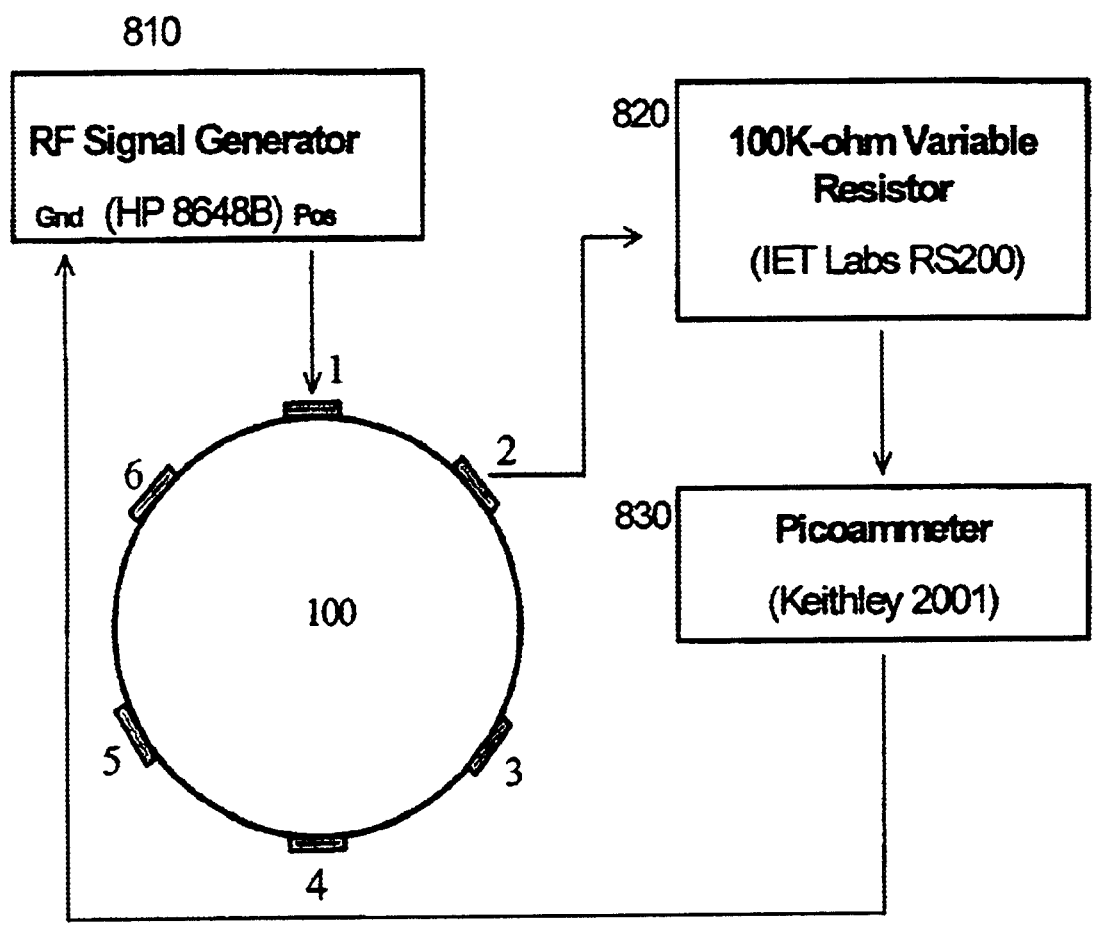
FIG. 8 is a block diagram of a current measurement circuit according to an embodiment of the invention.

FIGS. 6–8 illustrate the measurement of signals according to some embodiments of the invention. FIG. 6 illustrates the measurement of AC voltage. An RF signal generator 610 is connected to a 10 watt RF amplifier 620. The output of the amplifier 620 is connected in parallel to a 50 ohm load 630, to a first electrode 1 in contact with wood piece 100, and to a first channel of an oscilloscope 640. A second terminal 2 is connected to a second channel of the oscilloscope 640. Using this arrangement, differences in magnitude and phase of the signals at electrodes 1 and 2 can be seen. As discussed previously herein, these measurements are preferably repeated for all possible electrode pairs in each direction. The order in which the measurements are made is not important.

FIG. 7 illustrates measurement of the impedance of a wood piece 100. An impedance analyzer 710 includes a signal generator (not shown separately in FIG. 7). The output of the signal generator is applied to electrode 1 and the impedance between electrodes 1 and 2 is measured. As with the voltage, the impedance (magnitude and phase shift) is preferably measured for all possible electrode pairs in both directions.

FIG. 8 illustrates current measurement. The output of a signal generator 810 is applied to a first electrode 1 in contact with a wood piece 100. A second electrode 2 is connected to the signal generator 810 ground through a 100 Kohm variable resistor 820 and an ammeter 830, which measure the current. As above, the current measurement is repeated for all possible pairs of electrodes in both directions.

The radio frequency range of the TLDD ranges between DC and 1 GHZ. The dielectric signals have been applied to sending electrodes at two voltage levels. A high-power signal of 100 volts was applied with voltage and phase shift measured. Radio frequency signals were applied at a power of 1 volt by an impedance analyzer. (The 1 volt signal was chosen due to limitations of the impedance analyzer.)

The signal through clear normal wood at the receiving electrode depends on signal frequency, log diameter and moisture content. For the 100-volt application for the best performing electrode types and sizes tested, signal strength passed through clear wood with electrodes spaced at 60 degrees of arc has been approximately 35 volts at 500 KHz for a 12-inch diameter green log. This TLDD device preferably uses a frequency in the radio frequency range which is defined as any frequency lower than 1 GHZ.

For the purpose of knot detection in green logs, transmission of signals between electrodes with 60 degrees of arc has given the best results to date. This orientation appears to result in deep penetration of signals into the log. The received signal is strong enough to indicate the presence of wood of differential density in the 60-degree area of arc between the electrodes. Hidden knots to a depth of about 4 inches in a 10-inch diameter log have been successfully detected by the TLDD of the present invention. However, other numbers of electrodes resulting in either more or less than 60 degrees of arc separation may be employed.

In his Master of Science thesis entitled *Detection of knots in Logs by Finite Element Analysis*, published in April, 2002 (Department of Electrical Engineering, Mississippi State University) and incorporated by reference herein, Bikkina described results of experiments performed with the TLDD. Experiments were performed to determine the ability of the TLDD device and method to detect knots in green southern yellow pine log segments. Nine log segments, three from each of three trees were cut such that the knots were located in the approximate center of 2-foot long segments. A flexible elastic strap with 6 evenly-spaced electrodes was wrapped around log segment circumference. Circumferential scans of both clear and knot wood were obtained at 2-inch intervals along the log segment length. Radio frequency voltage of 100 volts applied to sending electrodes was sensed at receiving electrodes. All combinations of electrodes were tested, but only in a single direction. Thus, 14 electrode-pair measurements were collected for the 6 electrodes used in this testing. Only data on magnitude of the voltage of the radio frequency signal was collected. In addition to collecting data from the TLDD device itself, a finite element model with parameters corresponding to the imposed TLDD conditions was developed using the electromagnetic simulation option of the ANSYS finite modeling software.

Statistical analysis of both actual and simulated study results showed that it was possible to determine presence and size of knots within the 60 degree angles of arc corresponding to the areas defined by the 6 electrodes evenly spaced around the log segment circumference. In addition, there was an ability to estimate knot depth for both actual and simulated data.

However, determination of the angular position, termed displacement by Bikkina, of the knot between electrodes spaced apart by 60 degrees was not possible. The reason for this was indicated by ANSYS simulations showing that the magnitude of the signal between electrode pairs was influenced by the proximity of a knot to the sending or receiving electrode. That is, for a knot positioned directly between electrodes there was little difference in signal magnitude for a signal transmitted Electrode 1 to Electrode 2 or transmitted from Electrode 2 to Electrode 1. However, if a knot was closer to one of the electrodes, a substantial difference in signal strength resulted. For example, for a knot nearer to Electrode 1 than Electrode 2 the magnitude of the signal sent from Electrode 1 to Electrode 2 was much greater than for a signal sent from Electrode 2 to Electrode 1. These results indicated that for voltage in voltage out measurement, information on signal magnitude in both the 1 to 2 electrode direction and the 2 to 1 electrode direction are required to provide information adequate to determine knot displacement.

Further studies by Applicants for data taken in the same manner as Bikkina but for the additional data for voltage phase shift and impedance magnitude and phase shift were measured. In addition, the additional data required for bi-directional electrode sending and receiving was obtained for the voltage signal. The results of this data supported the Bikkina study findings.

Between neighboring electrodes separated by sixty degrees of arc, presence, area, and depth of knots were all found by Applicant to be significantly estimable variables. And, based on the additional data for voltage signals transmitted in both directions between electrodes, the knot displacement between electrodes was also significantly estimable.

A particular advantage of the TLDD of the present invention is its ability to make a direct estimate of knot depth by varying signal frequency based on voltage measurement. The above Initial research results indicate that knot depth can be estimated by examination of the relative magnitude of the capacitance signal between electrodes at various frequencies. Lower frequencies penetrate deeper into logs than higher frequencies. Application of several frequencies at the same scanning position allowed comparison of signal characteristics. For example, should a low frequency signal value indicate knot presence while a higher frequency signal value indicate no evidence of knot presence, one would conclude that this knot is relatively deep in the log.

In some embodiments of the TLDD, non-receiving electrodes (i.e., those electrodes other than the electrode to which the signal is applied and the electrode to which the measurement device is connected) are not grounded. Experiments by Applicants have shown that magnitude and phase shift of signals transmitted to the receiving electrode(s), whether grounded or ungrounded, are significantly reduced by this practice. However, some advantages are obtained from grounding of the non-receiving electrode(s) (e.g. noise reduction).

Data on magnitude and phase shift of current flow to the grounded receiving electrodes has been analyzed between 60-degree electrodes and has been shown to significantly reduce both magnitude and phase shift of current flowing to the receiving electrode(s). However, some advantages are obtained from grounding of the receiving electrode(s) (e.g., noise reduction). In addition, grounding is required for use of current. For this reason, the TLDD must ground the receiving electrode when current is used and may ground the receiving electrode(s) for voltage and impedance signals.

Because log diameters vary both in and between individual logs, the electrodes employed must be movable in order to maintain close contact with the log surface. Such movement constantly changes the distance between electrodes and will render the imaging problem more difficult. Presently, voltage and impedance differences at a predetermined angle and distance are used, and the differences in signal impedance and phase at the various frequencies are compared. When electrode movement occurs, algorithms will be applied to correct for relative electrode movement.

Lionheart, in *Annals of the New York Academy of Sciences*, (1999) 873: 466–471, shows that electrical imaging is unavoidably a three-dimensional problem, and for accurate location of anomalies in conductivity or permittivity it is essential to make measurements in more than one plane. Forward modeling and image reconstruction can then be carried out in three dimensions (Vauhkonen, *IEEE Trans Biomed Eng*, (1999) 46:1150–1160), incorporating any a priori knowledge such as upper and lower bounds on permittivity or smoothness of the surface of knots. The motion of the log through the electrode array is equivalent to measurement in multiple planes and this can also be exploited in TLDD.

Applicants have tested ½", 1", 2", and 3" circular electrode sizes and a large rectangular 1.5"×2.5" electrode size. With respect to knot differentiation, it was found that the smaller circular electrodes performed better. This is a surprising result because, for ECT, electrode capacitance is positively exponentially related to electrode area. Therefore, it would be expected that large electrodes would be more sensitive to the presence of anomalies such as knots. However, because knots are small, their effect when present between large electrodes may be less significant. For small electrodes, the knot may comprise a much larger portion of material between the electrodes. Therefore, despite a reduction in capacitance for smaller electrodes, their effectiveness for knot detection is superior. Smaller electrodes will also allow for increased resolution.

For larger anomalies in logs, cants, poles, timber or trees, large electrodes with higher capacitance will have superior performance. This is because such larger anomalies will tend to comprise a much larger proportion of the material between the electrodes.

Based on the results showing superiority of small electrodes for small anomalies and large electrodes for larger anomalies, use of both electrode sizes in a single system may be desirable. FIG. 4 shows one series of electrodes may be comprised of smaller circular electrodes while a second series may be comprised of larger rectangular electrodes.

Having now fully described the invention, it will be apparent to one of ordinary skill in the art that changes and modifications can be made thereto without departing from the spirit or scope of the invention as set forth herein. It is to be understood, therefore, that within the scope of the appended claims, the invention may be practiced otherwise than as specifically described herein.

What is claimed is:

1. An apparatus for detecting an anomaly in wood, the apparatus comprising:
   a signal generator;
   a first non-penetrating electrode connected to the signal generator, the first electrode being adapted to be placed in contact with the wood;
   a second non-penetrating electrode, the second electrode being adapted to be placed in contact with the wood, such that the first electrode and the second electrode are peripherally arranged around the wood; and
   a measurement device connected to the second electrode, the measurement device being configured to measure a parameter of a signal at different cross-sections the second electrode, whereby a three-dimensional location of an anomaly in the wood piece is detected based on the parameter.

2. The apparatus of claim 1, wherein the measurement device measures voltage.

3. The apparatus of claim 1, wherein the parameter is current and the measurement device is an ammeter.

4. The apparatus of claim 1, wherein the parameter is impedance and the measurement device is an impedance meter.

5. The apparatus of claim 1, wherein the magnitude of the parameter is measured.

6. The apparatus of claim 1, wherein the phase shift of the parameter is measured.

7. The apparatus of claim 1, wherein the signal generator is connectable to the second electrode and the measurement device is connectable to the first electrode.

8. The apparatus of claim 1, wherein the signal generator generates a signal including a plurality of frequencies and wherein the parameter is measured for each of the frequencies in order to determine a depth of a knot in the wood piece.

9. The apparatus of claim 1, wherein the electrodes are separated by approximately one hundred and eighty degrees.

10. The apparatus of claim 1, wherein at least one of the electrodes is movable.

11. The apparatus of claim 1, wherein at least one of the electrodes is a wire brush electrode.

12. The apparatus of claim 1, further comprising a plurality of electrodes that, together with the first and second electrode from a first series of electrodes, each of the electrodes in the first series being peripherally arranged around the wood, such that the electrodes are equidistant from each other.

13. The apparatus of claim 1, further comprising a second series of electrodes, each electrode of the second series being peripherally arranged around the wood such that the electrodes are equidistant from each other, a position of each electrode in the first series differing from a position of a nearest neighboring electrode in the second series by approximately one-half of the distance between the electrodes in the first series.

14. The apparatus of claim 1, wherein the first and second electrodes are part of a first series of electrodes, the apparatus further comprising a plurality of electrodes in a second series of electrodes, a size of an electrode in the first series being different from a size of an electrode in the second series.

15. The apparatus of claim 14, wherein electrodes in the first series have a round shape, electrodes in the second series have a rectangular shape, and the electrodes in the second series are larger than the electrodes in the first series.

16. The apparatus of claim 15, wherein an ammeter is connected to the electrodes in the first series and a measurement device for measuring voltage or impedance is connected to the electrodes in the second series.

17. The apparatus of claim 1, wherein the signal generator generates a radio frequency signal.

18. The apparatus of claim 1, wherein the wood is at least one of:
   a wood piece;
   a log;
   a cant;
   timber;
   a pole; and
   a tree.

19. The apparatus of claim 1, wherein the anomaly is at least one of:
   a knot;
   avoid;
   decay;
   differential density;
   differential moisture; and
   wood type.

20. The apparatus of claim 1, wherein the wood is machined to a shape allowing equidistant arrangement of electrodes peripherally around the wood.

21. A method for detecting a knot an anomaly an wood, the method comprising the steps of:
   placing a first non-penetrating electrode in contact with the wood;
   placing a second non-penetrating electrode in contact with the wood;

applying a first signal to the first electrode, such that the first electrode and the second electrode are peripherally arranged around the wood; and connecting a first measuring device to the second electrode to measure a first parameter at different cross-sections to detect a three-dimensional location of an anomaly in the wood.

22. The method of claim 21, wherein the first parameter as voltage.

23. The method of claim 21, wherein the first parameter is current.

24. The method of claim 21, wherein the first parameter is impedance.

25. The method of claim 21, wherein both magnitude and phase shift are measured for the first parameter.

26. The method of claim 21, further comprising the step of measuring a second parameter.

27. The method of claim 26, wherein the first parameter is voltage and the second parameter is current.

28. The method of claim 26, wherein the first parameter is voltage and the second parameter is impedance.

29. The method of claim 26, wherein the first parameter is voltage and the second parameter is voltage.

30. The method of claim 26, wherein the first parameter is voltage and the second parameter is phase shift.

31. The method of claim 26, wherein the first parameter is current and the second parameter is voltage.

32. The method of claim 26, wherein the first parameter is current and the second parameter is current.

33. The method of claim 26, wherein the first parameter is current and the second parameter is impedance.

34. The method of claim 26, wherein the first parameter is current and the second parameter is phase shift.

35. The method of claim 21, further comprising the step of moving the wood relative to the first electrode and the second electrode.

36. The method of claim 35, wherein at least one electrode is a wire brush electrode.

37. The method of claim 35, wherein the wood has an irregular surface and at least one electrode is movable such that the electrode may remain in contact with the irregular surface.

38. The method of claim 37, further comprising the steps of:

applying a second signal to the second electrode; and connecting the first measuring device to the first electrode to measure a third parameter.

39. The method of claim 38, wherein the third parameter is of a same kind as the first parameter.

40. The method of claim 21, wherein the signal is a direct current signal.

41. The method of claim 21, wherein the signal is a radio frequency signal.

42. The method of claim 41, wherein the radio frequency signal comprises a single frequency.

43. The method of claim 41, wherein the radio frequency signal comprises multiple frequencies, and wherein the first parameter is measured at a plurality of the multiple frequencies.

44. The method of claim 21, wherein the first electrode and the second electrode form at least part of a first series of electrodes, further comprising the steps of placing a second series of electrodes in contact with the wood, the second series of electrodes having a size different from the first series of electrodes.

45. The method of claim 44, wherein the second series of electrodes has a shape different from the first series of electrodes.

46. The method of claim 44, wherein the series of electrodes with a smaller size are used to measure current and the series of electrodes with a larger size are used to measure voltage.

47. The method of claim 44, wherein the series of electrodes with a smaller size are used to measure current and the series of electrodes with a larger size are used to measure impedance.

48. The method of claim 44, wherein electrodes in the first series are positioned in equidistant increments from other electrodes in the first series, electrodes in the second series are positioned in equidistant increments from other electrodes in the second series, and each electrode in the second series is offset with respect to the electrodes of the first series by approximately one half of a distance between the electrodes of the first series.

49. The method of claim 21, wherein the wood is at least one of:

a wood piece;

a log;

a cant;

timber:

a pole; and a tree.

50. The method of claim 21, wherein the anomaly is at least one of:

a knot;

a void;

decay;

differential density;

differential moisture; and wood type.

51. The method of claim 21, wherein the wood is machined to a shape allowing equidistant arrangement of electrodes peripherally around the wood.

52. A method for detecting a knot an anomaly in wood, the method comprising the steps of:

arranging a plurality of non-penetrating electrodes peripherally around of the wood piece, the plurality of electrodes placed in contact with the wood and forming a first series of electrodes;

applying a first signal to a first electrode of the plurality of electrodes;

connecting a measurement device to each of the other electrodes; and repeating the applying and measuring steps at a different cross-section for each of the other electrodes such that the first parameter is measured in both directions for each possible pair of electrodes, whereby a three-dimensional location of an anomaly in the wood is detected based on the first parameter.

53. The method of claim 52, wherein the electrodes are in contact with the wood.

54. The method of claim 52, wherein the connecting step is performed for each electrode sequentially, one electrode at a time.

55. The method of claim 54, wherein electrodes other than the first electrode and the electrode to which the measurement device is currently connected are grounded.

56. The method of claim 54, wherein electrodes other than the first electrode and the electrode to which the measurement device is currently connected are not grounded.

57. The method of claim 52, wherein the electrodes are separated by approximately equal increments.

58. The method of claim 52, wherein voltage is measured in the connecting step.

59. The method of claim 52, wherein current is measured in the connecting step.

60. The method of claim 52, wherein impedance is measured in the connecting step.

61. The method of claim 52, further comprising the step of measuring a second parameter.

62. The method of claim 52, wherein the electrodes have a width less than two inches.

63. The method of claim 52, wherein the electrodes have a width less than one inch.

64. The method of claim 52, wherein the electrodes have a width of approximately one half of an inch.

65. The method of claim 52, wherein the first signal includes a plurality of frequencies and wherein the first parameter is measured for each of the frequencies in order to determine a depth of an anomaly in the wood.

66. The method of claim 52, wherein the first electrode and the second electrode are movable.

67. The method of claim 52, wherein at least one of the electrodes is a wire brush electrode.

68. The method of claim 52, wherein the electrodes are approximately equal increments apart.

69. The method of claim 52, further comprising the steps of:

arranging a second series of electrodes peripherally around the wood; and repeating the applying and connecting steps for the second series of electrodes for each electrode in the second series in both directions for each possible pair of electrodes.

70. The method of claim 52, further comprising the step of forming at tomographic image depicting a density of the wood using measurements made during the connecting step.

71. The method of claim 52, wherein the electrodes are wire brush electrodes.

72. The method of claim 71, further comprising the steps of:

moving the wood relative to the wire brush electrodes; and performing the applying, connecting, and repeating steps at a plurality of locations along a length of the wood.

73. The method of claim 52, further comprising the step of forming a tomographic image of the wood using measurements obtained from the measurement device.

74. The method of claim 52, wherein the parameter is voltage.

75. The method of claim 52, wherein the parameter is current.

76. The method of claim 52, wherein the parameter is impedance.

77. The method of claim 52, wherein a width of the electrodes is approximately one half inch.

78. The method of claim 52, wherein the wood is at least one of:

a wood piece;

a log;

a cant;

timber;

a pole; and a tree.

79. The method of claim 52, wherein the anomaly is at least one of:

a knot;

a void;

decay;

differential density;

differential moisture; and wood type.

80. The method of claim 52, wherein phase shift is measured in the connecting step.

81. A method for detecting an anomaly in wood, the method comprising the steps of:

arranging a plurality of ungrounded non-penetrating electrodes peripherally around the wood, the plurality of electrodes placed in contact with the wood and forming a first series of electrodes;

applying a first signal to a first electrode of the plurality of electrodes;

connecting a measurement device to each remaining electrode of the plurality of electrodes, to measure a first parameter; and repeating the connecting step at a different cross-section whereby each remaining electrode becomes the first electrode such that the first parameter is measured at each remaining electrode, whereby a three-dimensional location of an anomaly in the wood is detected based on the first parameter.

82. A method for detecting an anomaly in wood, the method comprising:

arranging a plurality of non-penetrating electrodes peripherally around the wood, the plurality of electrodes placed in contact with the wood and forming a first series of electrodes;

applying a first signal to a first ungrounded electrode of the plurality of electrodes;

connecting a measurement device to each remaining grounded electrode of the plurality of electrodes to measure a first parameter with electrodes other than the first ungrounded electrode; and repeating the connecting step at a different cross-section whereby each remaining grounded electrode becomes the first ungrounded electrode such that the first parameter is measured at each remaining grounded electrode, whereby a three-dimensional location of an anomaly in the wood is detected based on the first parameter.

83. A method for detecting an anomaly in wood, the method comprising the steps of;

arranging a plurality of ungrounded non-penetrating electrodes peripherally around the wood, the plurality of electrodes placed in contact with the wood and forming a first series of electrodes;

applying a first signal to a first electrode of the plurality of electrodes;

grounding a second electrode opposite to the first electrode;

connecting a measurement device to each of the electrodes other than the first and second electrodes, to measure a first parameter;

repeating the signal application to a first electrode and grounding of a second adjacent electrode to all possible remaining adjacent electrode pairs; and measuring a first parameter at a different cross-section at all electrodes other than each adjacent first and second electrodes comprising the electrode pairs, whereby a three-dimensional location of an anomaly In the wood is detected based on the first parameter.

84. A method for detecting an anomaly in wood, the method comprising:

arranging a plurality of non-penetrating electrodes peripherally around the wood, the plurality of electrodes placed in contact with the wood and forming a first series of electrodes;

applying a first signal to a first electrode of the plurality of electrodes;

grounding a second electrode opposite to the first electrode;

connecting a measurement device to each of the electrodes other than the first and second electrodes, to measure a first parameter;

repeating the signal application to a first electrode and grounding of a second opposite electrode to all possible remaining opposite electrode pairs; and measuring a first parameter at a different cross-section at all electrodes other than each opposite first and second electrodes comprising the electrode pairs, whereby a three-dimensional location of an anomaly in the wood is detected based on the first parameter.

* * * * *